even though United States Patent [19]

Brown

[11] 4,251,522
[45] * Feb. 17, 1981

[54] PHENOXYBENZYLPHOSPHONIUM SALTS AND DERIVATIVES THEREOF AND USE AS FUNGICIDES

[75] Inventor: Michael J. Brown, Randolph Township, Morris County, N.J.

[73] Assignee: GAF Corporation, New York, N.Y.

[*] Notice: The portion of the term of this patent subsequent to Nov. 6, 1996, has been disclaimed.

[21] Appl. No.: 8,075

[22] Filed: Jan. 31, 1979

Related U.S. Application Data

[62] Division of Ser. No. 861,205, Dec. 16, 1977, Pat. No. 4,162,312.

[51] Int. Cl.³ .......................... A01N 57/22; C07F 9/54
[52] U.S. Cl. ..................................... 424/214; 424/211; 424/214; 424/217; 568/11
[58] Field of Search ............................... 424/214, 217; 260/606.5 F

[56] References Cited

U.S. PATENT DOCUMENTS 3,642,989  2/1972  Martin et al. ..................... 424/211
3,804,950  4/1974  Diamond ........................... 424/211

Primary Examiner—Allen J. Robinson

Attorney, Agent, or Firm—James Magee, Jr.; Marilyn J. Maue

[57] ABSTRACT

The fungicidal compounds having the formula:

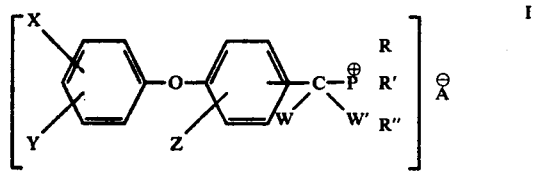

wherein $A^{\ominus}$ is a halogen anion; X, Y and Z are each independently hydrogen, a halogen atom or a haloalkyl radical of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The invention also relates to the method of preparing said compounds, together with their formulations as agricultural products and fungicidal use thereof.

14 Claims, No Drawings

PHENOXYBENZYLPHOSPHONIUM SALTS AND DERIVATIVES THEREOF AND USE AS FUNGICIDES

This is a division of application Ser. No. 861,205, filed Dec. 16, 1977, now U.S. Pat. No. 4,162,312.

This application relates to a new class of chemical compounds, a process for their preparation and the fungicidal application of said compounds, utilized either alone or in chemical formulations with a carrier to be applied to a plant as a spray or dust.

The compounds of this invention find utility as fungicides which are ecologically safe and leave no toxic residue in the plant or on the soil.

It is an object of this invention to provide new and useful chemical compounds which can be employed as fungicides which are not harmful to the environment.

Another object of this invention is to provide an economically feasible method for the preparation of the present compounds.

Yet another object is to provide novel fungicides for eradication of, and protection of plants against, fungus infection.

Still another object of this invention is to provide formulations for the present compounds in agricultural applications to plants.

These and other objects of the present invention will become apparent from the following description and disclosure.

According to this invention, there is provided phosphonium salt compounds having the formula:

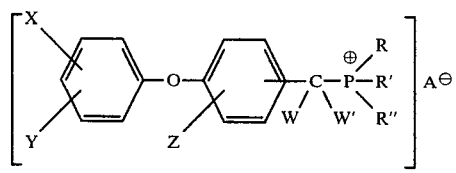

wherein $A^\ominus$ is a halogen anion; X, Y and Z are each independently hydrogen, a halogen atom or a haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The halogen referred to in the above phosphonium salt compounds is fluorine, chlorine, bromine or iodine.

Of the above group of compounds, the preferred fungicides are those wherein at least one of the substituents X, Y or Z is a halogen or a perhaloalkyl group, e.g. a trifluoromethyl group; R, R', R" are the same and are lower alkyl or phenyl radicals and W is hydrogen, —CHO or —CHN (R''')$_2$ and W' is hydrogen or, when W is —CHN(R''')$_2$, then W' is a bond forming a double bond between W and the C of the group

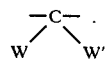

Most preferred of the fungicidal compounds are those of the group having the formula:

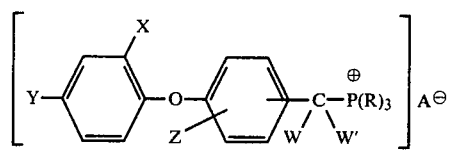

wherein X and Z are independently —Cl or —H; Y is —CF$_3$ or —H; R is phenyl or butyl; W is —H or —CH.N(CH$_3$)$_2$ and W' is —H or, when W is —CH.N(CH$_3$)$_2$, then W' is a bond forming a double bond between W and C in the above structural formula.

In general, the phenoxy benzyl phosphonium compounds of the present invention may be prepared according to the reaction illustrated by the following equation I, wherein the reactants in each stage are contacted in a mole ratio of between about 1:2 and about 2:1, preferably stochiometric amounts of the required reactants, and the various reactions are effected at a temperature between about 0° C. and about 180° C. under from about 5 to about 25 psig pressure, more desirably between about 5° C. and about 150° C. under atmospheric pressure. Stage (2) of the reaction is beneficially carried out in the presence of a peroxy type catalyst, e.g. benzoyl peroxide. Under most preferred conditions, reaction (3) is carried out at between about 10° C. and 35° C. under atmospheric pressure. The reaction, usually carried out over a period of from about 30 minutes to about 4 hours, is effected in liquid phase with an organic solvent; chloroform being illustrative of the solvents selected for stage (3) of the reaction with a phosphine. It is to be understood, however, that other solvents, such as xylene, toluene, bromoform, methyl isobutyl ketone, dichloromethane, carbontetrachloride, ethanol, propanol, dimethylformamide, 2-methoxyethyl ether, or other solvents conventionally employed for quaterinization reactions, may be substituted, in the whole or in part, for chloroform in stage (3) of the reaction illustrated by Equation I.

Since the product of stage (1) between a halogenated benzene and the metal oxide of a toluene and the product of stage (2) between a halogenated phenyl benzyl ether and N-bromosuccinimide are known, the novel stage in process of the present invention may be considered to reside in stage (3) where phenoxybenzylbromide or other halide such as the corresponding chloride or iodide, is reacted with a trisubstituted phosphine to provide the novel quaternized product.

Since the phenoxybenzyl halide reactants of stage (3) in Equation I are generally known in the art, alternative methods for the preparation of the correspondingly substituted phenoxy benzylphosphonium quaternized salts will become apparent to those skilled in the art from this disclosure. For example, free radical halogenation of the phenoxybenzyl product of stage (1) in the absence or presence of a catalyst such as a metal halide or UV light can be effected to produce the corresponding halomethyl analogue or reactant of stage (3).

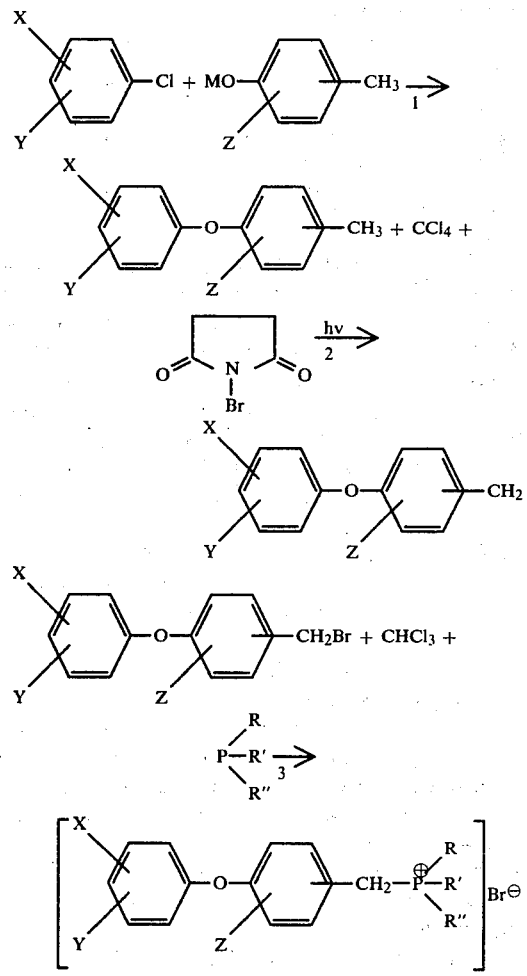

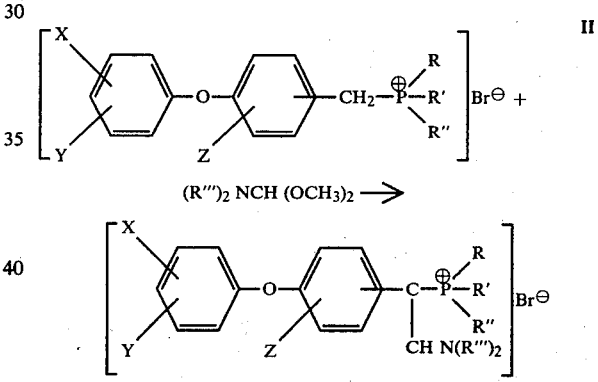

The preferred alkali metal halides are the iodide or fluoride of sodium or potassium.

The phase-transfer reaction is carried out at a temperature between about 5° C. and about 125° C. preferably between about 10° C. and about 100° C., under atmospheric conditions. The substituted halide anion product is recovered by drawings off the lower liquid product phase or by decanting the upper liquid aqueous alkali metal halide or ammonium halide phase. The product is then isolated by evaporating the lower product phase to dryness, washing the product with water, followed by evaporation to dryness. The washing and drying operation can be repeated as desired.

To obtain the amino substituted phosphonium salt of the present invention, the final product of Equation I, or the corresponding chloride, fluoride, or iodide anion of the product of Equation I, is reacted with an aminodimethoxymethane in an anhydrous alcoholic solution, e.g. an anhydrous solution of ethanol, propanol, butanol, pentanol, or another inert organic solvent. This reaction is carried out at a temperature of between about 10° C. and about 180° C. under from about 5 psig to about 30 psig, preferably at a temperature between about 80° C. and about 140° C. under atmospheric pressure. The following Equation II exemplifies such a viable process for the preparation of the amino substituted phosphonium compounds of the present invention using bromine anion for purposes of illustration.

In the above reaction, M represents an alkali metal, such as Li, Na, K or Ca; Na or K being preferred, X, Y, Z, R, R' and R" having the meaning set forth above for Formula I. The product of stage 3 can be isolated and recovered by distilling off solvent and then triturating the product with petroleum ether, cyclohexane or other inert trituating agent. The corresponding chloride anion may be obtained from the final product of Equation I by a substitution reaction in which the bromine of the product reacts with an excess of sodium- or potassium-chloride in aqueous solution. The substitution reaction is effected under atmospheric pressure at a temperature of between about 5° C. and about 150° C. in the presence of chloroform or any other suitable water-immisible inert solvent.

The corresponding fluoride or iodide anions may be obtained from the product of Equation I by phase-transfer. Generally, to obtain the various halide anions of the present invention, the product of reaction (3) in Equation I is dissolved in chloroform or other suitable solvent, such as bromoform or any water-immisible inert solvent. To this solution an aqueous alkali metal halide or ammonium halide solution, wherein the halide of the alkali metal or ammonium salt is capable of replacing the bromine anion of the phosphonium compound, is added with agitation until two liquid layers are formed; usually within a period of from 15 minutes to 4 hours.

In the above equations, X, Y, Z, R, R', R" and R''' having the meaning set forth in Formula I of the preceeding disclosure.

The above amino substituted product is recovered from the reaction mixture by evaporation to dryness to remove alcoholic by-product and trituration with petroleum ether, cyclohexane or any other inert agent conventionally employed for forming a fine particulate solid or powder.

To obtain the aldehyde derivative of the phosphonium salt of the present invention, the product of Equation II, or the corresponding fluoride, chloride or iodide anion of said product, is reacted with an aqueous solution of mineral acid such as a 2 to 50% solution of HCl, H$_2$SO$_4$, HNO$_3$, etc., at a temperature of between about 25° C. and about 100° C. under from about 5 psig to about 30 psig; preferably between about 50° C. and about 80° C. under atmospheric pressure. The corresponding aldehyde substituted phosphonium compound is formed within a period of from about 15 minutes to about 1.5 hours and is recovered from the reaction mixture by extraction with chloroform or another inert organic solvent conventionally employed for removing acid impurities. The solvent is then evaporated and the product triturated with a suitable agent, such as petroleum ether.

The following Equation III illustrates such a viable process for the preparation of the aldehyde derivative of the halogenated phenoxybenzyl phosphonium compound.

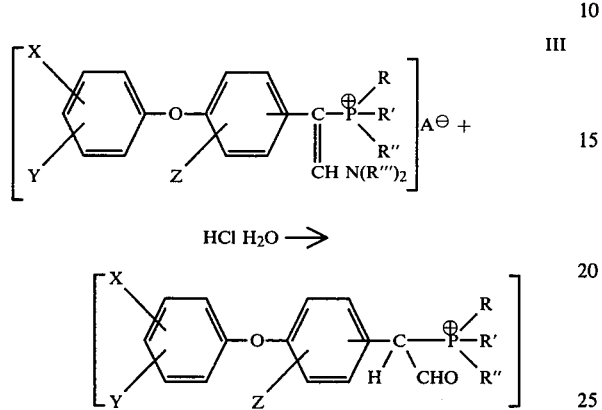

The product of Equation III may be converted into the corresponding dehydrohalogenated compound as shown in Equation IV. The conversion is effected by passing the aldehyde substituted phosphonium compound (e.g. the product of Equation III) downwardly through an anion exchange column (e.g. Amberlite CG-4B, 200-400 mesh) in an alcohol solution, e.g. a methanol solution, at ambient temperature. The product is then isolated by evaporation to dryness followed by trituration with cyclohexane or petroleum ether or any other conventional trituration liquid. As indicated, the product of Equation IV exists in equilibrium.

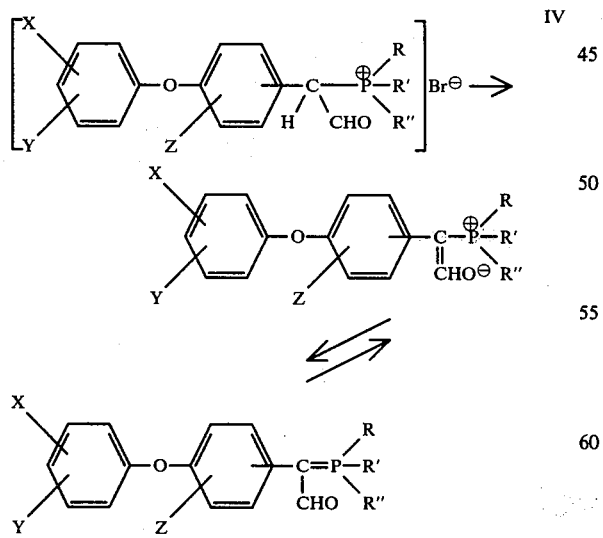

The following compounds shown in Table I are representative of the novel compounds of the present invention.

TABLE I

| Compound Number | Structure | °C. Melt Pt. |
|---|---|---|
| 1 | 2-Cl-C₆H₄-O-C₆H₄-CH₂P⁺(C₄H₉)₃ Br⁻ | 145-7 |
| 2 | 2-Cl-C₆H₄-O-C₆H₄-CH₂P⁺(C₄H₉)₃ Br⁻ | 115-9 |
| 3 | CF₃-C₆H₄-O-C₆H₄-CH₂P⁺(C₄H₉)₃ Br⁻ | 88-90 |
| 4 | CF₃-C₆H₄-O-C₆H₄-CH₂P⁺(C₂H₅)₃ Br⁻ | 144-6 |
| 5 | 2-Cl-C₆H₄-O-C₆H₄-CH₂P⁺(C₂H₅)₃ Br⁻ | 144-6 |
| 6 | 2-Cl-C₆H₄-O-C₆H₄-CH₂P⁺(C₂H₅)₃ Br⁻ | 119-21 |
| 7 | 2-Cl-C₆H₄-O-C₆H₄-CH₂P⁺(C₂H₅)₃ Br⁻ | 151-3 |
| 8 | 2-Cl-C₆H₄-O-C₆H₄-CH₂P⁺(C₄H₉)₃ Br⁻ | 88-90 |
| 9 | 2-Cl-C₆H₄-O-C₆H₄-CH₂-P⁺(C₆H₅)₃ Br⁻ | 243-50 |
| 10 | 2-Cl-C₆H₄-O-C₆H₄-CH₂P⁺(C₆H₅)₃ Br⁻ | 105 |
| 11 | CF₃-C₆H₄-O-C₆H₄-CH₂P⁺(C₄H₉)₃ Br⁻ | 112-3 |
| 12 | CF₃-C₆H₄-O-C₆H₄-CH₂P⁺(C₂H₅)₃ Br⁻ | 152-5 |
| 13 | CF₃-C₆H₄-O-C₆H₄-CH₂P⁺(C₆H₅)₃ Br⁻ | 145-9 |
| 14 | 2-Cl-C₆H₄-O-C₆H₄-CH₂P⁺(C₆H₅)₃ Br⁻ | 118-22 |
| 15 | CF₃-C₆H₄-O-C₆H₄-CH₂P⁺(C₆H₅)₃ Br⁻ | 91 |

TABLE I-continued

| Compound Number | Structure | °C. Melt Pt. |
|---|---|---|
| 16 | CF$_3$–⟨⟩–O–⟨⟩–Cl, Cl, CH$_2$P$^⊕$(C$_4$H$_9$)$_3$ Br$^⊖$ | 90 |
| 17 | CF$_3$–⟨⟩–O–⟨⟩–Cl, Cl, CH$_2$P$^⊕$(C$_6$H$_5$)$_3$ Br$^⊖$ | 100 |
| 18 | CF$_3$–⟨⟩–O–⟨⟩–Cl, Cl, CH$_2$P$^⊕$(C$_2$H$_5$)$_3$ Br$^⊖$ | 134–7 |
| 19 | ⟨⟩–O–⟨⟩(Cl), CH$_2$P$^⊕$(C$_4$H$_9$)$_3$ Br$^⊖$ | 84–8 |
| 20 | ⟨⟩–O–⟨⟩(Cl), CH$_2$P$^⊕$(C$_6$H$_5$)$_3$ Br$^⊖$ | 74–8 |
| 21 | ⟨⟩–O–⟨⟩(Cl), CH$_2$P$^⊕$(C$_2$H$_5$)$_3$ Br$^⊖$ | <25 |
| 22 | ⟨⟩(Cl)–O–⟨⟩–CH$_2$P(C$_4$H$_9$)$_3$ $^⊕$Cl$^⊖$ | 159–60 |
| 23 | ⟨⟩(Cl)–O–⟨⟩–C(=CH N(CH$_3$)$_2$)–$^⊕$P(C$_6$H$_5$)$_3$ Br$^⊕$ | 50–8 |
| 24 | ⟨⟩(Cl)–O–⟨⟩–CH(–CHO)–$^⊕$P(C$_6$H$_5$)$_3$ Br$^⊖$ | 184–8 |
| 25 | ⟨⟩(Cl)–O–⟨⟩–C(=CHO$^⊖$)–$^⊕$P(C$_6$H$_5$)$_3$ | 75 |

A. PREPARATION OF COMPOUNDS 1–21

Of the above compounds, 1–21 were prepared by reacting the corresponding halogenated phenyl tolyl ether with N-bromo-succinimide in the liquid phase where carbon tetrachloride is employed as the solvent. The reaction was carried out in a glass reactor with constant mixing and irradiation with ultraviolet light in the presence of a catalytic amount of benzoyl peroxide. After conversion was effected, the corresponding halogenated phenoxybromotoluene was recovered by filtering to remove the insoluble by-product, i.e. succinimide, and then distilling off the carbon tetrachloride. The desired intermediate product, i.e. brominated ether derivative, was then purified by vacuum distillation. The recovered intermediate product was then dissolved in chloroform or xylene and reacted with phosphine in a sealed glass reactor with constant stirring to obtain the product corresponding to the Compound Number shown in the following Table II. Other conditions of the reactions are also reported in Table II.

TABLE II

PREPARTION OF COMPOUNDS 1 THROUGH 21 LISTED IN TABLE I

| Compd. No. | gms of halogenated phenyl tolyl ether | reactn conds. temp. (°C./press. (psig)/ time (hrs) | gms. N-bromo succinimide /mls. CCl$_4$ solvent | gms. halogenated phenoxy bromotoluene deriv./mls. solvent | gms of phosphine | reactn. conds. temp. (°C.)/press. (psig)/ time (hrs) | Method of Recovery |
|---|---|---|---|---|---|---|---|
| 1. | 175g of ⟨⟩(Cl)–O–⟨⟩(CH$_3$) | 77/- atmospheric/24 | 185.1/500 | 29.7/50 xylene | 22.3g of P(C$_4$H$_9$)$_3$ | 25/- atmospheric/2 | filtration followed by trituration with petroleum ether |
| 2. | 112g of ⟨⟩(Cl)–O–⟨⟩–CH$_3$ | 77/- atmospheric/28 | 118/700 | 10/100 xylene | 7.4g of P(C$_4$H$_9$)$_3$ | 138/- atomospheric/8.5 | filtration followed by trituration with xylene and then petroleum ether |
| 3. | 26g of F$_3$C–⟨⟩–O–⟨⟩(CH$_3$) | 77/- atmospheric/18 | 19.8/100 | 7/25 CHCl$_3$ | 4.2g of P(C$_4$H$_9$)$_3$ | 25/- atmospheric/16 | evaporation to dryness followed by trituration with petroleum ether |
| 4. | 26g of F$_3$C–⟨⟩–O–⟨⟩(CH$_3$) | 77/- atmospheric/18 | 19.8/100 | 5/25 CHCl$_3$ | 3g of P(C$_2$H$_5$)$_3$ | 25/- atmospheric/20 | Same as #3 |

TABLE II-continued

PREPARTION OF COMPOUNDS 1 THROUGH 21 LISTED IN TABLE I

| Compd. No. | gms of halogenated phenyl tolyl ether | reactn conds. temp. (°C./press. (psig)/ time (hrs) | gms. N-bromo succinimide /mls. CCl$_4$ solvent | gms. halogenated phenoxy bromotoluene deriv./mls. solvent | gms of phosphine | reactn. conds. temp. (°C.)/press. (psig)/ time (hrs) | Method of Recovery |
|---|---|---|---|---|---|---|---|
| 5. | 80g of [2-Cl-phenyl 2-methylphenyl ether] | 77/- atmospheric/24 | 78.2/400 | 10/50 CHCl$_3$ | 4.4g of P(C$_2$H$_5$)$_3$ | 25/- atmospheric/20 | Same as #3 |
| 6. | 112g of [2-Cl-phenyl 4-methylphenyl ether] | 77/- atmospheric/28 | 118/700 | 5/25 CHCl$_3$ | 2.2g of P(C$_2$H$_5$)$_3$ | 25/- atmospheric/20 | Same as #3 |
| 7. | 175g of [2-Cl-phenyl 3-methylphenyl ether] | 77/- atmospheric/24 | 185.1/500 | 5/25 CHCl$_3$ | 2.2g of P(C$_2$H$_5$)$_3$ | 25/- atmospheric/20 | Same as #3 |
| 8. | 80g of [2-Cl-phenyl 2-methylphenyl ether] | 77/- atmospheric/24 | 78.2/400 | 10/50 CHCl$_3$ | 7.6g of P(C$_4$H$_9$)$_3$ | 25/- atmospheric/20 | Same as #3 |
| 9. | 112g of [2-Cl-phenyl 4-methylphenyl ether] | 77/- atmospheric/28 | 118/700 | 10/50 CHCl$_3$ | 10.3g of P(C$_5$H$_6$)$_3$ | 25/- atmospheric/20 | Same as #3 |
| 10. | 80g of [2-Cl-phenyl 2-methylphenyl ether] | 77/- atmospheric/24 | 78.2/400 | 10/50 CHCl$_3$ | 10.3g of P(C$_6$H$_5$)$_3$ | 25/- atmospheric/20 | Same as #3 |
| 11. | 51.2g of [4-F$_3$O-phenyl 2-methylphenyl ether] | 77/- atmospheric/22 | 41.6/200 | 10/50 CHCl$_3$ | 6.7g of P(C$_4$H$_9$)$_3$ | 25/- atmospheric/20 | Same as #3 |
| 12. | 51.2g of [4-F$_3$C-phenyl 2-methylphenyl ether] | 77/- atmospheric/22 | 41.6/200 | 10/50 CHCl$_3$ | 3.9g of P(C$_2$H$_5$)$_3$ | 25/- atmospheric/20 | Same as #3 |
| 13. | 26g of [4-F$_3$C-phenyl 3-methylphenyl ether] | 77/- atmospheric/18 | 19.8/100 | 10/50 CHCl$_3$ | 8.7g of P(C$_6$H$_5$)$_3$ | 25/- atmospheric/20 | Same as #3 |

TABLE II-continued
PREPARATION OF COMPOUNDS 1 THROUGH 21 LISTED IN TABLE I

| Compd. No. | gms of halogenated phenyl tolyl ether | reactn conds. temp. (°C./press. (psig)/ time (hrs) | gms. N-bromo succinimide /mls. $CCl_4$ solvent | gms. halogenated phenoxy bromotoluene deriv./mls. solvent | gms of phosphine | reactn. conds. temp. (°C.)/press. (psig)/ time (hrs) | Method of Recovery |
|---|---|---|---|---|---|---|---|
| 14. | 52g of 2-chloro-phenyl 3-methylphenyl ether (Cl ortho; CH₃ meta) | 77/- atmospheric/24 | 185.1/500 | 10/50 $CHCl_3$ | 10.3g of $P(C_6H_5)_3$ | 25/- atmospheric/20 | Same as #3 |
| 15. | 51.2g of 4-(trifluoromethyl)phenyl 2-methylphenyl ether ($F_3C$—⌬—O—⌬—$CH_3$) | 77/- atmospheric/22 | 41.6/200 | 10/50 $CHCl_3$ | 8.7g of $P(C_6H_5)_3$ | 25/- atmospheric/20 | Same as #3 |
| 16. | 64.8g of $F_3C$—⌬(Cl)—O—⌬(Cl)—$CH_3$ | 77/- atmospheric/48 | 39.5/200 | 10/50 $CHCl_3$ | 3.5g of $P(C_4H_9)_3$ | 25/- atmospheric/20 | Same as #3 |
| 17. | 64.8g of $F_3C$—⌬—O—⌬(Cl)—$CH_3$ with Cl on left ring | 77/- atmospheric/48 | 39.5/200 | 10/50 $CHCl_3$ | 4.7g of $P(C_6H_5)_3$ | 25/- atmospheric/20 | Same as #3 |
| 18. | 66.8g of $F_3C$—⌬(Cl)—O—⌬(Cl)—$CH_3$ | 77/- atmospheric/48 | 39.5/200 | 10/50 $CHCl_3$ | 2.1g of $P(C_2H_5)_3$ | 25/- atmospheric/20 | Same as #3 |
| 19. | 45.5g of phenyl-O-(Cl, CH₃)phenyl ether | 77/- atmospheric/23 | 41/200 | 10/50 $CHCl_3$ | 7.5g of $P(C_4H_9)_3$ | 25/- atmospheric/20 | Same as #3 |
| 20. | 45.5g of phenyl-O-(Cl, CH₃)phenyl ether | 77/- atmospheric/23 | 41/200 | 6.5/50 $CHCl_3$ | 6.3g of $P(C_6H_5)_3$ | 25/- atmospheric/20 | Same as #3 |
| 21. | 45.5g of phenyl-O-(Cl, CH₃)phenyl ether | 77/- atmospheric/23 | 41/200 | 6.5/50 $CHCl_3$ | 2.8g of $P(C_2H_5)_3$ | 25/- atmospheric/20 | Same as #3 |

B. PREPARATION OF COMPOUND 22

Compound 1 in the above Table I (5 g) was dissolved in 25 ml of chloroform and introduced into a reactor. To this solution was added a saturated solution of sodium chloride (100 ml) to form a 2 phase mixture and the resulting mixture was agitated at a temperature of 25° C. for 0.5 hour. The lower layer was drawn off, dried over anhydrous magnesium sulfate, filtered and evaporated to dryness to recover 4.2 g of 2-chlorophenoxy-3'-benzyltributylphosphonium chloride.

The corresponding chlorides of compounds 2 through 21 are prepared in a similar manner with concentrated aqueous solutions of potassium chloride or sodium chloride, e.g. saturated solutions by reacting at a temperature of from 25° C. to 100° C., e.g. 25° C.

under atmospheric pressure and recovering the product as set forth above.

It is to be understood that the corresponding fluoride or iodide phosphonium salts of compounds 1 to 21 are similarly prepared by substituting saturated aqueous solutions of potassium fluoride or iodide or sodium fluoride or iodide in the above example.

C. PREPARATION OF COMPOUND 23

Compound 14 in Table I (5 g) was dissolved in 30 ml of anhydrous propanol and introduced into a reactor. This solution was heated to 110° C. and 5.5 g of dimethylaminodimethoxymethane was added. The reaction mixture was maintained at 110° C. and agitated for 32 hours at atmospheric pressure. The resulting reaction mixture was then evaporated to remove the solvent and triturated with 100 ml petroleum ether, after which it was dried to provide 3.5 g of product.

It is to be understood that any of the corresponding fluoride, chloride or iodide phosphonium salts of compound 1 or any such salts of compounds 2 through 21 can be substituted in the above preparation C to provide the corresponding halogen-containing phenoxy styrylamino triphenyl phosphonium halide.

D. PREPARATION OF COMPOUND 24 OF TABLE I

The above Compound 23 (22 g) was introduced into a reactor wherein it was contacted with 165 ml of a 2 normal aqueous solution of hydrochloric acid at a temperature of 60° C. under atmospheric pressure for a period of 0.75 hour. The resulting product was then recovered by extraction with 200 ml of chloroform at room temperature and the chloroform vaporized by vacuum evaporation. The product is then triturated with petroleum ether to yield 10 g of product of over 95% purity.

It is to be understood that any of the corresponding fluoride, chloride or iodide phosphonium salts of the halogen-containing phenoxy styryl amino phosphonium bromides described in preparation C can be substituted in the above Preparation D to provide the corresponding aldehyde of the phosphonium salt.

E. PREPARATION OF COMPOUND 25 OF TABLE I

The above compound 24 (5 g) was dissolved in methanol (25 ml) and passed through a column of amberlite anion exchange resin (8.5 g of CG-4B, 200-400 mesh). After eluting the column with a further 20 ml of methanol the combined effluent was evaporated to dryness and the resulting oil triturated with cyclohexane (50 ml) and petroleum ether (50 ml) to yield 3 g of product.

It is to be understood that any of the corresponding fluoride, chloride or iodide phosphonium salts of the halogen-containing aldehyde described in preparation D can be substituted in the above preparation E to provide the corresponding dehydrohalogenated compound.

In their fungicidal use, the compounds of the present invention can be applied alone or can be employed in combination with an adjuvant in either liquid or solid form. The compositions or formulations containing the compounds of the present invention are prepared by admixing one or more of the present fungicides with the adjuvant including diluents, extenders, carriers or conditioning agents to provide compositions in the form of finely-divided particulate solids, granules, pellets, wetable powders, dusts, solutions and aqueous dispersions or emulsions. The concentration of the compound in the carrier is preferably between about 5 and about 50 weight percent. Illustrative of the granular solid carriers and extenders which may be employed include the talcs, clays, diatomaceous earth, silica, pumice, sulphur, wallnut or coconut flour, wood dust, tobacco dust, charcoal and the like. Illustrative of the liquid carriers and extenders are water, propyleneglycol, N-methylpyrrolidone, benzene, xylene, cyclohexane and other liquid paraffins, acetone, methylethylketone, ethylketone, and other known extenders and carriers which may be employed singly or in combination.

The formulations may also include a minor amount up to 5% of a surfactant which includes wetting agents, dispersing agents, suspending agents, and emulsifying agents. Typical of this group are the polyoxyethylene derivatives of fatty acid esters, imidazolines, etc. It is also to be understood that the formulations of the present invention may include other active components to achieve additional biocidal effect. Such combinations include mixtures of the present compounds with, e.g. Ethephon, triacontanol, Phosphon, Nitrofen or other biologically active compounds.

In selecting the appropriate rate of application of the present fungicides, it should be understood that the precise rates will be somewhat dependent upon the mode of application, such as soil incorporation, and pre-emergent or post-emergent plant treatment and foilar dusting or drench. Generally, for fungicidal effects, the present compound or mixture of the present compound is applied in amounts of from about 0.05 to about 25 pounds per acre, or more. Preferably, applications of from about 0.1 to about 10 pounds per acre of active ingredient is employed. The concentration of the present compound either employed alone or in a formulation or composition is between about 5 ppm and about 10,000 ppm preferably between about 5 ppm and about 1,000 ppm, per plant, or an effective dosage for at least 80% plant response for the effect desired.

Having thus generally described the invention, reference is now had to the accompanying examples which serve to illustrate preferred and specific embodiments, but which are not to be construed as unduly limiting to the scope of the present invention as defined in the foregoing specification and in the appended claims. In the following examples, all amounts are by weight unless otherwise indicated. It is to be understood, that any of the foregoing compounds of this invention, as defined in Formula I which are not exemplified in the following examples, can be substituted therein to provide the fungicidal benefits of the present invention.

EXAMPLES 1-25

The compounds listed in the following Table III were tested as fungicides against the highly pernicious bean rust, bean mildew, rice spot and early blight of tomatoes as representative species of fungi.

For each test compound, three groups of four 4.5 week-old bean seedlings from the same seed source, growing in sterlized soil under uniform conditions were separately sprayed to drench with 250 ppm, 65 ppm and 33 ppm concentrations of the indicated test compound and labeled Group C, $C_1$ and $C_2$ respectively. The formulations of test compounds employed for spraying were prepared in aqueous solution as reported in Examples 1-26.

The sprayed plants of Group C, $C_1$ and $C_2$ were allowed to dry and each plant was then atomized with a suspension of bean rust spores in aqueous solution with 0.5% of Tween 20 as a surfactant. The spores on the infected plants were incubated in a humidity cabinet at 70°-75° F. for 24 hours and then held in the greenhouse for three days during which time fungus lesions on plant leaves would normally appear. An unsprayed, infected group of bean plants of the same species, under otherwise similar conditions, developed lesions on all leaves leading to demise of the plants within one month.

For each of the compounds tested, two groups of four 4.5 week-old rice seedlings of the star bonnet variety from the same seed source, growing in sterlized soil under uniform conditions were separately sprayed to drench with 250 ppm and 33 ppm concentrations of each of the test compounds listed in Table III and labeled Group D and $D_1$ respectively. The formulations of test compounds employed for spraying were again prepared in a manner similar to those employed above as reported in Examples 1-26.

The sprayed plants were allowed to dry and each plant was then atomized with a suspension of rice spot spores in aqueous solution. The infected plants were incubated in a humidity cabinet at 70°-75° F. for 24 hours and then held in the greenhouse for three days during which time brown spots would normally appear on leaves and stems of plants. An unsprayed, infected group of rice plants of the same species, under otherwise similar conditions, developed severe spotting and died within 2 weeks.

For each compound tested, one group of four 4.5 week-old tomato seedlings from the same seed source and growing in sterlized soil under uniform conditions were separtely sprayed to drench with 33 ppm concentrations of each of the test compounds listed in Table III and the plants in this group labeled Group E. The formulations of test compounds employed for spraying were prepared in a manner similar to those employed above as reported in Examples 1-26.

The sprayed plants were allowed to dry and each plant was then atomized with a suspension of early blight fungus in aqueous solution containing 1% of orange juice concentrate. The infected plants were then incubated in a humidity cabinet at 70°-75° F. for 24 hours and then held in the greenhouse for three days during which time leaf spotting occurred. An unsprayed, infected group of tomato plants of the same species, under otherwise similar conditions developed severe spotting and defoliation leading to the death of the plants within one month.

For each compound tested, one group of 4.5 week-old bean seedlings of the variety used in Group C was sprayed to drench 250 ppm concentration of the indicated test compounds and labeled Group F. The formulations of test compounds employed for spraying were prepared as discussed above and the sprayed plants were dried and infected as previously described, except that the pathogen for Group F was Bean Mildew spores. The infected plants were then subjected to above described incubation and activity of the fungicidal spray in % inhibition of fungus noted four days after infection.

The efficacy of test compounds on plants in Groups C, $C_1$, $C_2$, D, $D_1$, E and F plants is reported in the following Table III in % of activity indicated. As in the foregoing, the test compound numbers correspond to the numbers assigned to the specific compounds illustrated in Table I.

TABLE III

| | | FUNGICIDAL ACTIVITY | | | | | | | | | |
|---|---|---|---|---|---|---|---|---|---|---|---|
| | | % Control of Fungi | | | | | | | | | |
| | | 250 ppm Concentration | | | 33 ppm Concentration | | | 65 ppm Concentration | | | | |
| Example No. | Test Compound No. | Bean Mildew (F) | Bean Rust (C) | Rice Spot (D) | Bean Rust ($C_1$) | Rice Spot ($D_1$) | Tomato E. Blight (E) | Bean Rust % Eradication ($C_2$) | Bean Rust % Residual ($C_2$) | Bean Rust % Resid. ppm Spray Conc. | | |
| | | | | | | | | | | 260 | 33 | 8 |
| 1 | 1 | 80 | 90 | 65 | — | — | — | — | — | | | |
| 2 | 2 | 90 | 90 | 85 | 75 | 90 | 64 | 40 | 40 | | | |
| 3 | 4 | 80 | 100 | 70 | — | 90 | — | — | — | | | |
| 4 | 5 | 35 | 100 | 90 | 80 | 70 | 50 | — | 65 | | | |
| 5 | 6 | 80 | 100 | 50 | — | — | — | — | — | | | |
| 6 | 7 | 70 | 100 | 90 | 90 | 75 | 0 | — | 65 | | | |
| 7 | 8 | 80 | 100 | 60 | — | — | — | — | — | | | |
| 8 | 9 | 40 | 100 | 80 | 100 | 65 | 0 | — | 100 | | | |
| 9 | 10 | 50 | 100 | 80 | 95 | 55 | — | — | 100 | | | |
| 10 | 11 | 70 | 70 | 90 | — | 80 | 40 | — | — | | | |
| 11 | 12 | 45 | 80 | 80 | 65 | 70 | 0 | — | — | | | |
| 12 | 13 | 65 | 100 | 80 | 100 | 75 | 50 | — | 100 | | | |
| 13 | 22 | 70 | 85 | 90 | 75 | 75 | 0 | — | 80 | | | |
| 14 | 14 | 75 | 100 | 85 | 100 | 65 | 0 | — | 100 | | | |
| 15 | 15 | 10 | 100 | 90 | 100 | 65 | 0 | 65 | 100 | | | |
| 16 | 16 | 40 | 100 | 90 | 90 | 80 | 60 | — | 80 | | | |
| 17 | 17 | 60 | 100 | 90 | 90 | 80 | 0 | — | 45 | | | |
| 18 | 18 | 60 | 95 | 100 | 75 | 60 | — | — | — | | | |
| 19 | 19 | 60 | 90 | 80 | 70 | 90 | 0 | — | — | | | |
| 20 | 20 | 30 | 90 | 80 | 95 | 90 | 5 | — | 50 | | | |
| 21 | 3 | 80 | 100 | 50 | — | — | — | — | — | | | |
| 22 | 23 | 80 | 100 | 90 | 100 | 90 | 10 | 40 | 90+ | 100 | 90 | 60 | 40 |
| 23 | 21 | 85 | 60 | 80 | — | 70 | 10 | — | — | | | |
| 24 | 24 | 15 | 100 | 70 | — | — | — | — | — | | | |
| 25 | 25 | 45 | 75 | 80 | 40 | 45 | — | — | — | | | |
| 26 | Phosphon | 60 | 55 | 90 | 85 | 65 | 0 | — | 25 | | | |

It is to be understood that any of the other fungicides falling within the scope of Formulae I or II or listed in Table I can be substituted in the above Examples of Table III to provide similar results for control of fungi.

What is claimed is:

1. The compound having the formula:

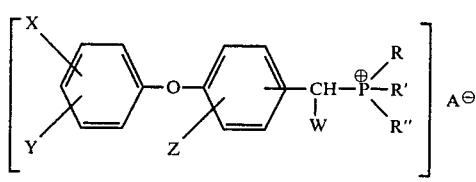

wherein A⊖ is a halogen anion; X, Y and Z are each independently hydrogen, a halogen atom or haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; and W is hydrogen, or —CHO.

2. The compounds of claim 1 wherein R, R' and R" are phenyl radicals; X is hydrogen and Y is a substituent other than hydrogen.

3. The compounds of claim 1 wherein R, R' and R" are the same and are lower alkyl of $C_1$ to $C_6$ carbon atoms.

4. The compound of claim 1 having the formula:

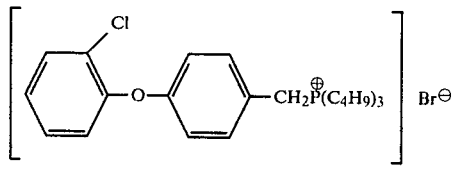

5. The compound of claim 1 having the formula:

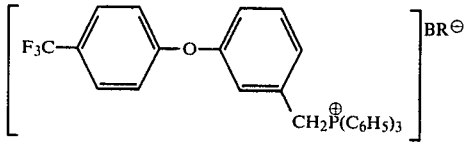

6. The compound of claim 1 having the formula:

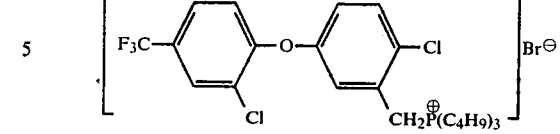

7. The compound of claim 1 having the formula:

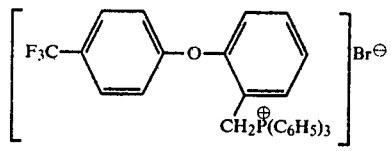

8. The compound of claim 1 wherein A⊖ is a halogen anion the structure of the compound is:

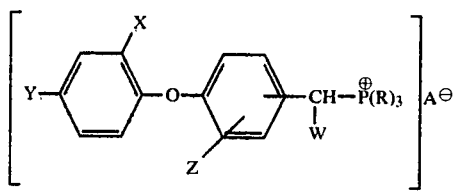

wherein X and Z are independently —Cl or —H; Y is —CF$_3$ or —H; R is phenyl or butyl; and W is —H or CHO.

9. The process of controlling fungus infection in plants which comprises treating said fungus infection with a fungicidally effective amount of at least one compound of claim 1.

10. The process of claim 9 wherein said compound is employed in a composition including an inert carrier wherein the concentration of said compound is between about 8 ppm and about 10,000 ppm.

11. The process of claim 10 wherein the composition is applied at a rate of between about 0.05 and about 25 lbs./acre.

12. The process of claim 10 wherein the compound is mixed with a carrier in a concentration of between about 30 ppm and about 3,000 ppm and is applied at a rate of between about 0.1 and about 10 lbs./acre.

13. The process of claim 10 wherein said carrier is a liquid.

14. The process of claim 10 wherein said carrier is a particulate solid.

* * * * *